United States Patent [19]

Russek

[11] Patent Number: 5,395,301
[45] Date of Patent: Mar. 7, 1995

[54] KINESTHETIC SYSTEM FOR PROMOTING RHYTHMIC BREATHING BY TACTILE STIMULATION

[76] Inventor: Linda G. Russek, 2701 N. Ocean Blvd., Apt. 708, Boca Raton, Fla. 33431

[21] Appl. No.: 192,788

[22] Filed: Feb. 7, 1994

Related U.S. Application Data

[63] Continuation-in-part of Ser. No. 860,724, Mar. 30, 1992, abandoned.

[51] Int. Cl.$^6$ ................... A61H 31/00; A61M 21/00
[52] U.S. Cl. ................... 601/41; 601/19; 601/103; 600/27
[58] Field of Search ............ 601/41, 43, 1, 18, 19, 601/97, 103, 101, 102, 84

[56] References Cited

U.S. PATENT DOCUMENTS

| | | | |
|---|---|---|---|
| 2,771,069 | 11/1956 | Baron | 128/28 |
| 3,263,677 | 8/1966 | Pastrick | 128/28 |
| 3,454,000 | 7/1969 | Bird et al. | 128/28 |
| 3,802,417 | 4/1974 | Lang | 128/716 |
| 3,991,304 | 11/1976 | Hillsman | 128/720 X |
| 4,149,531 | 4/1979 | Tanaka et al. | 128/57 X |
| 4,195,802 | 4/1980 | Gilson et al. | 340/407 |
| 4,481,944 | 11/1984 | Bunnell | 128/203.17 |
| 4,606,328 | 8/1986 | Thoman | 600/27 |
| 4,607,624 | 8/1986 | Jefferson | 128/24.2 |
| 4,694,839 | 9/1987 | Timme | 128/721 |
| 4,977,889 | 12/1990 | Budd | 128/30.2 |
| 5,088,475 | 8/1992 | Steffewsmeier | 128/57 X |

FOREIGN PATENT DOCUMENTS

| | | | |
|---|---|---|---|
| 1399717 | 7/1975 | United Kingdom | 128/716 |
| 1436032 | 5/1976 | United Kingdom | 128/716 |

OTHER PUBLICATIONS

BMI Baselines, vol. 6, No. 1, 1991, Bio-Medical Instruments, Inc.
BMI Baselines, vol. 7, No. 1, 1992, Bio-Medical Instruments, Inc.

Primary Examiner—Richard J. Apley
Assistant Examiner—John P. Leubecker
Attorney, Agent, or Firm—Hamilton, Brook, Smith & Reynolds

[57] ABSTRACT

A desired pattern, such as a desired breathing pattern for a respiratory ventilator, is encouraged by the operation of a kinesthetic device, preferably by a kinesthetic device which emulates human touch.

16 Claims, 5 Drawing Sheets

KINESTHETIC SYSTEM FOR PROMOTING RHYTHMIC BREATHING BY TACTILE STIMULATION

This application is a continuation-in-part of application Ser. No. 07/860,724, filed Mar. 30, 1992, now abandoned.

FIELD OF THE INVENTION

The present invention relates to a kinesthetic breathing performance system and method.

BACKGROUND OF THE INVENTION

To use a respiratory ventilator, a patient has to adapt or change his or her ingrained breathing pattern, as explained, e.g., in U.S. Pat. No. 3,991,304 to Hillsman, the disclosure of which is incorporated herein by reference. The Hillsman patent addresses this problem by providing a system which displays an ideal breathing pattern on a video screen, which can be watched and followed by the patient. But this is not a satisfactory solution, particularly since respiratory patients are often not able to see, or at least not able to respond well to visual stimuli. Also, the Hillsman approach does nothing to reduce anxiety and disorientation, which are the natural result of being connected to a ventilator.

Other related prior art patents include U.S. Pat. No. 2,771,069 to Baron, U.S. Pat. No. 2,821,189 to Hofmann, U.S. Pat. No. 3,403,674 to Alimanestiano, U.S. Pat. No. 3,547,106 to Bornmann, U.S. Pat. No. 3,552,388 to Zelenka, U.S. Pat. No. 3,730,173 to Deaton, U.S. Pat. No. 4,064,869 to Defares et al., and U.S. Pat. No. 4,984,568 to Persaud, the disclosures of which are incorporated herein by reference.

U.S. Pat. No. 2,771,069 to Baron discloses a bed which is pivoted in synchronization with a respiratory device to promote a desired respiration pattern. In operation, the head of the bed is positioned downwardly so that a patient can exhale air. When the bed is tilted up, air is inhaled by the patient. However, the system disclosed in the Baron patent is complicated and cumbersome, and it would increase a patient's anxiety and disorientation rather than promote a relaxed and ultimately fruitful response.

Similarly, the Defares patent discloses an apparatus for regulating breathing. The apparatus has a tone generator for producing audible tones for regulating the breathing patterns of a patient. The Defares device includes a sensor which is attached to a patient's chest containing a tube which is alternately expanded and contracted to the rhythm of the patient's breathing. When the breathing rhythm is out of synchronization with a clock control counter, a hyperventilation signal is produced which activates a generator. The generator tones are alternately progressively increased and decreased to produce two different tones signalling abnormal breathing. However, a recovering patient's responses to auditory tones may be severely limited by medication, causing an inability to concentrate. Additionally, noises made by other equipment might interfere with the patient's ability to hear tones.

The Bornmann patent discloses a device which imparts mechanical stimulation to arouse an infant which has stopped breathing. However, that mechanical stimulation fails to promote rhythmic breathing. The Hofmann patent discloses a respiration stimulation device where breathing rhythms are controlled by applying low frequency current to alternate muscle groups controlling the inspiration and exhalation muscles. The Deaton patent discloses a device for monitoring the respiration and/or heartbeat of a patient through any conventional device such as an apnea monitor. When respiration appears to be abnormal, a stream of pressurized air is directed against the patient's body. The Zelenka patent discloses a baby-patting machine. The Alimanestiano and Persaud patents disclose massaging devices.

SUMMARY OF THE INVENTION

In view of the foregoing, it should be apparent that there still exists a need in the art to provide a satisfactory system for helping a recovering patient control his/her breathing in accordance with a medically desired pattern and a need for a system which can help a patient learn and sustain a desired breathing pattern, while at the same time providing a gentle calming influence to reduce that patient's anxiety and disorientation. Finally, the prior art fails to provide a device which promotes rhythmic breathing without audio interference or visual interruption.

It is therefore, an object of this invention to provide a kinesthetic producing apparatus or method that promotes a desired psychological effect on a user by emulating human touch.

It is also an object of this invention to produce the kinesthetic effect in response to timing signals from a machine which evidences a user's psycho/physiological condition.

It is another object of this invention to provide a method and apparatus for establishing a patient's breathing pattern by stroking a ventilator patient's body, which, for example, would include an arm, wrist or shoulder, in rhythm with the desired breathing pattern. Patients appear to be most responsive to this physical or tactile stimulation, and are able to synchronize their breathing with the sensed cyclical mechanical motion. The stroking motion also has a gentle soothing effect.

It is also an object of this invention to provide a device which produces a kinesthetic motion that can be set to a desired heart rate, breath rate or any other rate that feels comfortable.

It is yet a further object of this invention to provide kinesthetic biofeedback which initiates a touch signal to the body of a patient in response to the signal generated by any machine, such as the electrocardiogram heart rate signal, or a blood pressure, or breath rate signal or a muscle contraction signal whereby the kinesthetic motion is prompted by the signal from each device rather than being prompted continuously so as to calm or stabilize the patient only when necessary.

It is yet an additional object of this invention to use a kinesthetic effect as an alarm, such as to wake or remind a user, or as a meditation or sleep inducement device where the rate and pressure of the kinesthetic effect can be varied, as desired.

It is yet another object of the invention to provide a kinesthetic touch system where the rate of reciprocation can be programmed in advance. Moreover, the kinesthetic device pressure can also be adjusted.

It is a further object of the invention to provide a kinesthetic device which is portable. It can also be worn comfortably under a patient's clothing.

Briefly described, these and other objects of the invention are carried out in its apparatus aspects by a breathing performance system which kinesthetically provides cyclical or rhythmic breathing encouragement or relaxation to a patient. The tactile stimulation is provided by a portable mechanical device which emulates human touch in synchronization with the desired breathing pattern set in a device.

The invention is carried out in accordance with its method aspects by locating a kinesthetic device with respect to a patient. The device is then cyclically operated in synchronization with a desired breathing pattern thereby encouraging the patient to breathe in a desired breathing pattern.

Other features of the present invention will be apparent from the following detailed description and drawings which illustrate preferred embodiments of the invention.

DETAILED DESCRIPTION OF THE PREFERRED EMBODIMENTS

Figure 1:
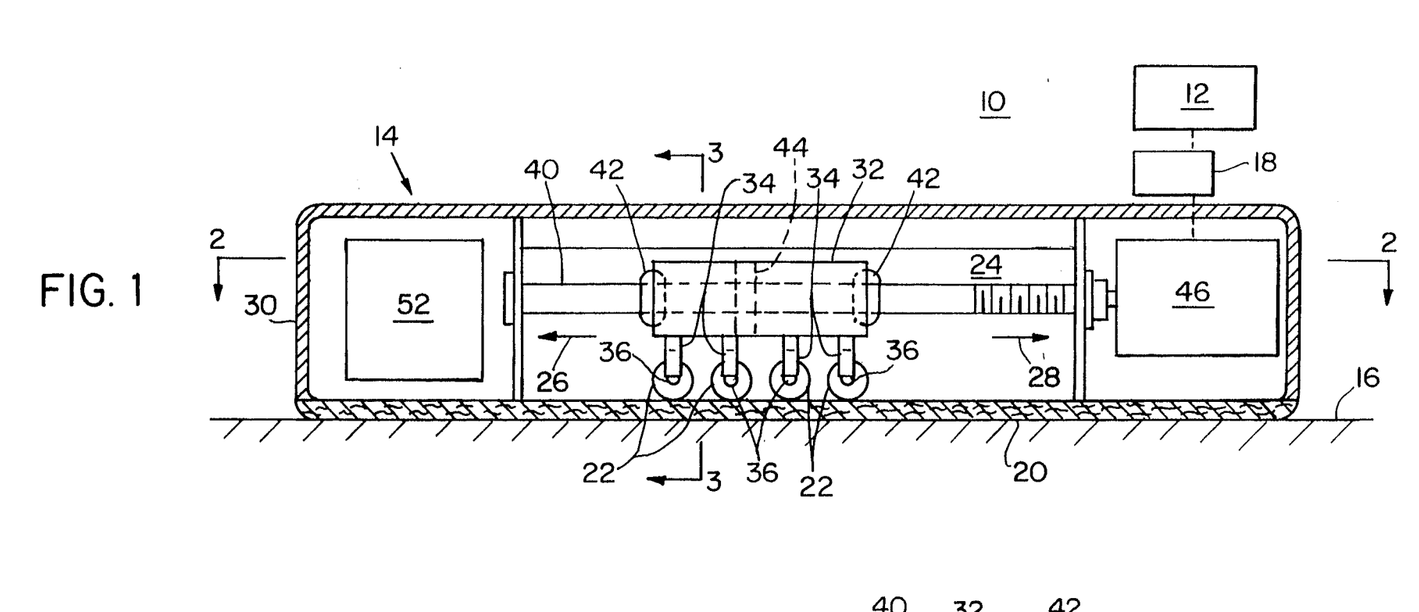
FIG. 1 is a schematic cross-sectional side view of a breathing performance system in accordance with a first embodiment of the present invention.

Referring now to the drawings, wherein like reference numerals represent like elements, there is shown in FIG. 1 a preferred embodiment of the invention used with a respiratory ventilator. However, numerous other applications for this invention are contemplated which will also be described as further embodiments. The respiratory ventilator system, which is constructed in accordance with the principles of the present invention, is designated generally by reference numeral 10.

Figure 6:
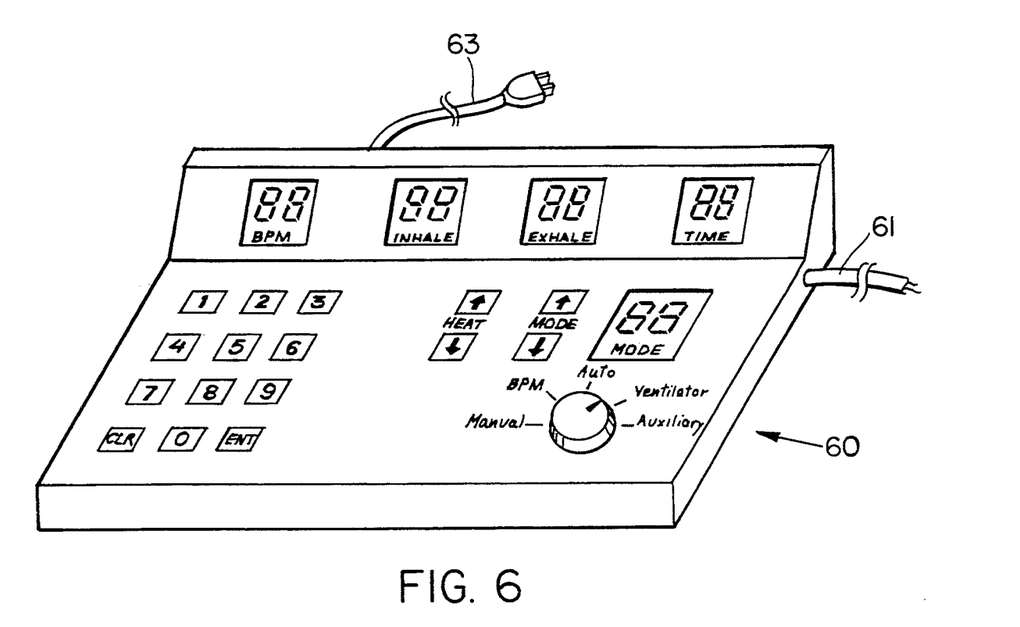
FIG. 6 is a perspective view of a stand alone control console.
Figure 7:
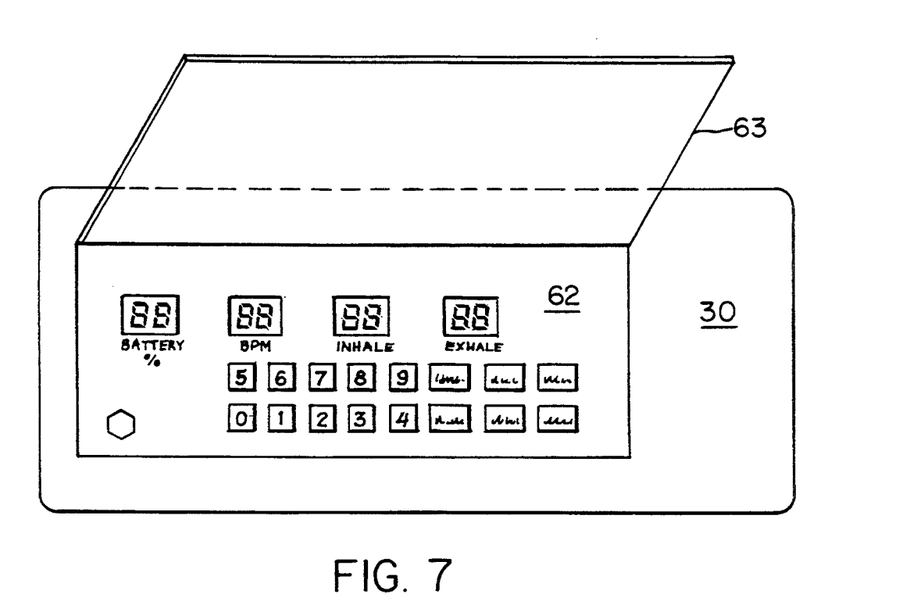
FIG. 7 is a top view of a control console incorporated into a kinesthetic device.

The respiratory ventilator system 10 includes a respiratory ventilator 12, a portable kinesthetic device 14 for providing tactile stimulation to the body 16 of a patient, and a controller 18 operatively connected to an output of the ventilator 12 for synchronizing the operation of the device 14 with the cyclical operation of the ventilator 12. The control means 18 can be electrical, mechanical or based on any other known technology. Details of one example of controller 18 are shown in FIGS. 6–7 with respect to console 60.

Figure 2A:
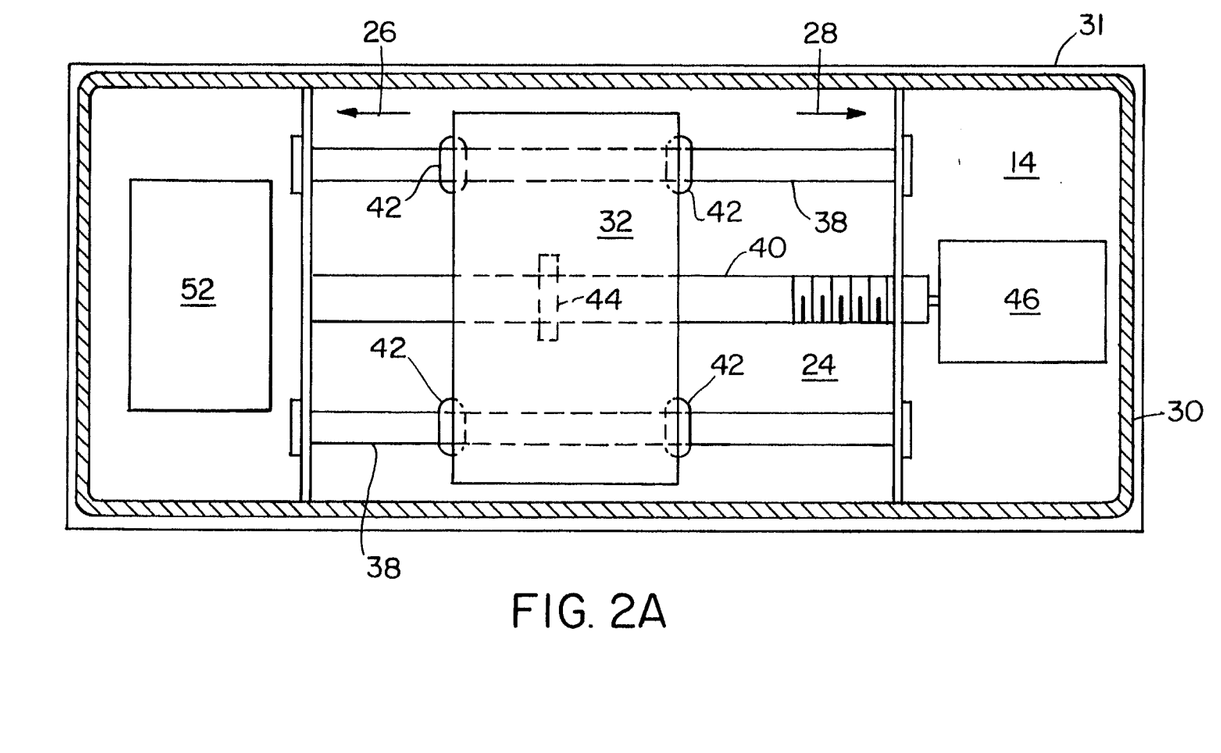
FIG. 2A is a cross-sectional view taken along the line 2—2 of FIG. 1.
Figure 2B:
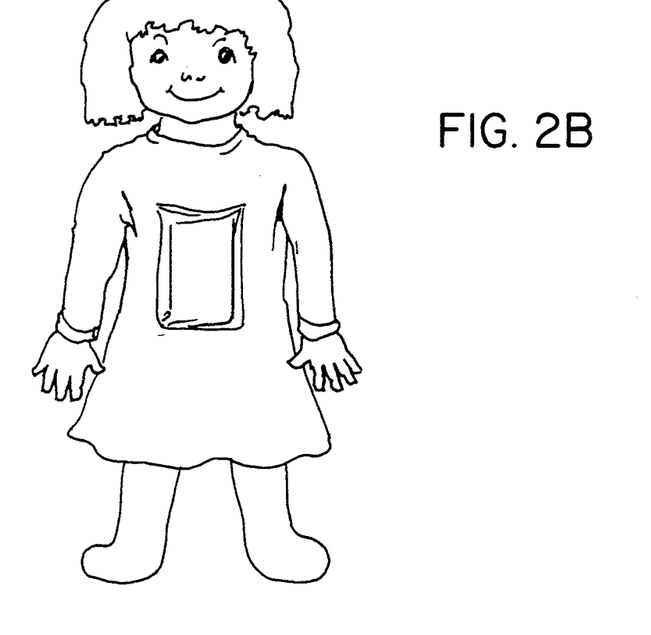
FIG. 2B illustrates the kinesthetic device of FIG. 1 in use in a second embodiment of the invention.

The kinesthetic device 14 is formed of a flexible pad 20, rollers 22, and a transmission means 24 for moving the rollers 22 back and forth in the directions indicated by arrows 26 and 28. The elements of the kinesthetic device 14 are contained within a cushioned sterilizable case 30. The device is fully enclosed in a sterilizable covering 31, as shown in FIG. 2A. The casing is releasably attached to the patient's body 16 (such as the patient's arms, legs or torso) by flexible tape, VELCRO ® brand, hook and loop fastener, belts or any other desirable strap (not illustrated). For pediatric use, a stuffed toy animal or doll or any other appropriate design or decoration (not illustrated) can be substituted for the external casing 31 so that the kinesthetic device 14 is located within the toy, animal, doll or other device, as shown in FIG. 2B while the controller 18 is mounted on the back of the doll (not shown). As a result of this arrangement, the kinesthetic device can calm a young patient. Alternatively, the toy, doll, animal or other device is mounted on the kinesthetic device covering 31 so that the device 14 is externally located.

Figure 2C:
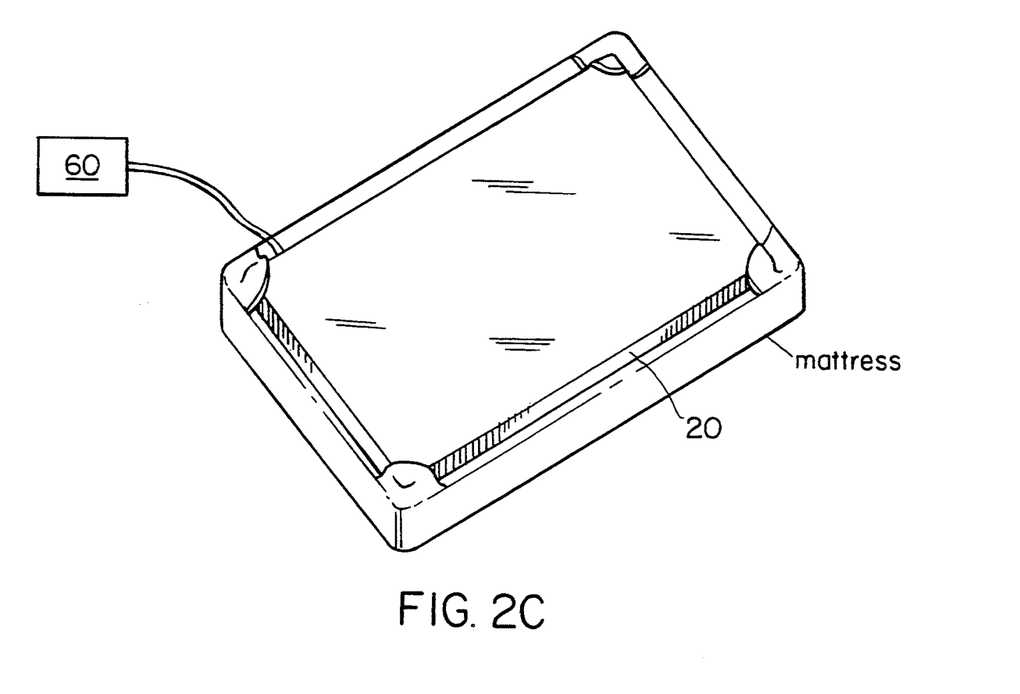
FIG. 2C illustrates the kinesthetic device of FIG. 1 in use in a third embodiment of the invention.

Moreover, the device 14 can be provided in or with a mattress cover pad. In this application, as shown in FIG. 2C, the device 14 is sufficiently proportioned to provide a kinesthetic effect substantially across the mattress.

For portability and to emulate human touch, the kinesthetic device 14 is light weight. Additionally, the case 30 is waterproof and electric shock proof in order to avoid any shock to the patient. The covering 31 may be connected to the case 30 by hook and loop type connectors (not illustrated) so as to be exchangeable for a new clean covering or for sterilization after one or more uses. Other conventionally known connectors may be used to attach covering 31 to case 30.

The device 14 is proportioned to easily fit under a user's shirt. This easy portability provides the user with numerous applications. For example, the user can wear the device to promote relaxation, to reduce blood pressure or to relieve stress. The device can also be worn to bed so that it can wake the wearer gently at a programmed hour, without disturbing others. Alternately, the kinesthetic device can be used to soothe the wearer—thus promoting sleep. Other applications include use of the device for sports or musical training, for birthing training in pre-labor classes or for use in conjunction with any equipment or biofeedback devices.

In the ventilator application, the ventilator 12 is operated according to a desired breathing pattern and the transmission means 24 follows this pattern. In other words, the pattern is the output of the ventilator translated and communicated by the controller 18 to the kinesthetic device 14. This control pattern causes the rollers 22 to move back and forth against the pad 20. As a result, tactile stimulation is provided to the body 16 in synchronization with the desired breathing pattern.

Figure 3:
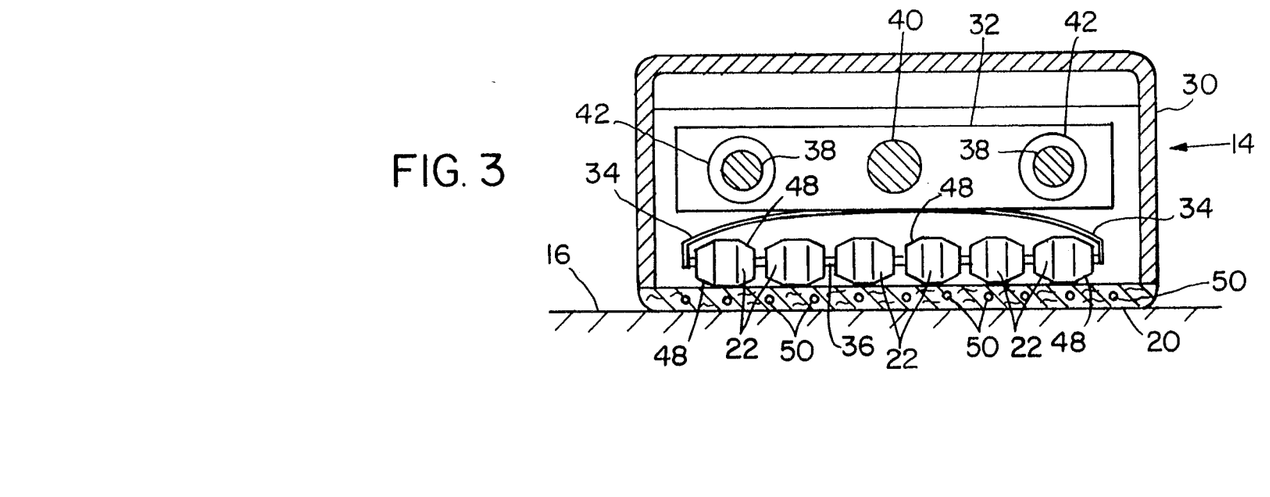
FIG. 3 is a cross-sectional view taken along the line 3—3 of FIG. 1.

The transmission means 24 is formed of a head unit 32 which is connected to the rollers 22 by leaf spring supports 34 and flexible rods 36 (FIG. 3). There are two round shafts 38 for slidably supporting the head unit 32, and a central threaded shaft 40 for driving the head unit 32 back and forth. Preferably, the shafts 38 pass through respective bushings 42. These bushings 42 prevent binding and reduce friction.

The shaft 40 is threaded into a nut 44 (FIG. 2) which is fixed with respect to the head unit 32. Thus, alternating clockwise and counterclockwise rotation of the shaft 40 causes the head unit 32 to move back and forth in the directions 26 and 28. The torque for rotating the shaft 40 is provided by a motor 46. The motor 46 is controlled by the synchronizing means 18. Preferably, the motor 46 is insulated to control noise, to avoid electric shock and to reduce breakage from handling.

Preferably, the pad 20 is made of a soft, flexible material that will transmit the "feel" of the rollers 22 as they travel back and forth. Preferably, as shown in FIG. 3, the device 14 has means for controlling the temperature of the pad 20 to promote patient comfort and to provide a calming effect. For example, the pad 20 may have integral heating elements 50 for gently heating the patient's skin. To emulate human touch, the pad 20 may be formed of suede, ultrasuede or a soft leather, although other soft materials may be suitable, particularly if a hypoallergenic material is desired. Considerations in selecting the material for the covering 31 include sterility and durability within the expected environment of use, and compatibility with various medical conditions, such as trauma infection and/or burns.

The rollers 22 are freely rotatably supported by the four flexible rods 36. The opposite ends of the rods 36 are held in place by the respective leaf spring supports 34, as illustrated in FIG. 3. The flexibility of the rods 36 and the supports 34 is such that the rollers 22 deflect inwardly and follow the contour of the flexible pad 20 as the pad 20 follows the contour of the patient's body 16. Preferably, each individual roller 22 has bevelled edges 48 to prevent binding as the flexible rods 36 are deflected inwardly. Preferably, the leaf spring supports 34 are independently connected to the movable head unit 32. Such independent suspension allows the rollers 22 to smoothly traverse any surface irregularities on the patient's body 16.

As an alternate embodiment, a small breath biofeedback machine can be used. The device comprises a vibrating beeper without rollers that can be properly instructed to receive messages from electrodes measuring muscular contractions placed on both the chest and abdomen. This device can be used with any other breath monitoring system. A digital clock and episode counter then measures the number of episodes of erratic or chest breathing during the course of time period and records it in real time (much like a Halter monitor). However, this device would be inconspicuous, it would measure the breath rate rather than the electrocardiogram, and it would alert the wearer to take a deep breath, to clam down and to lower the breath to the abdomen. The beeper could be worn inside the shirt or on the belt like an ordinary beeper.

Figure 4:
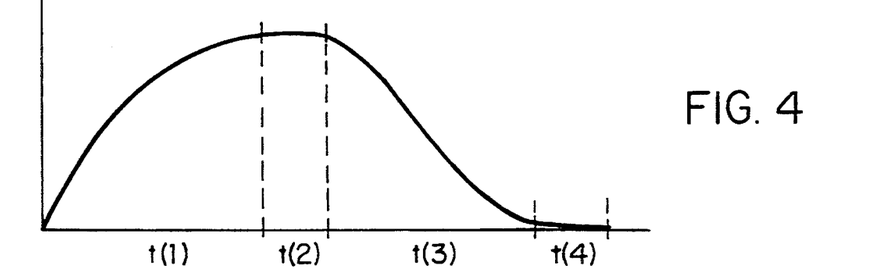
FIG. 4 is a graph of a desired breathing pattern.
Figure 5:
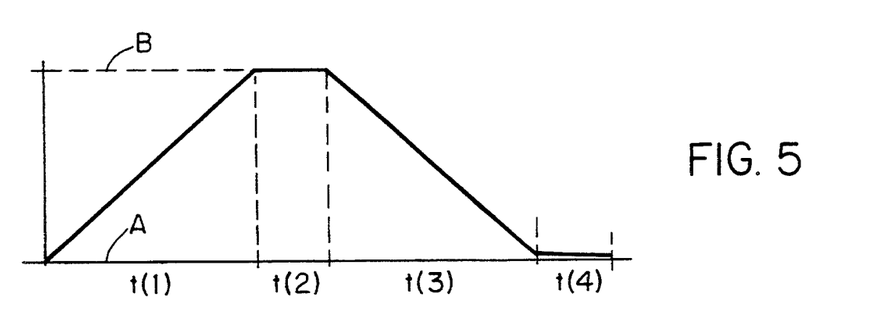
FIG. 5 illustrates the operation of the breathing performance system of FIG. 1.

To better illustrate the method of the present invention, the human breathing cycle can be broken down into four approximate phases, as illustrated in FIG. 4, wherein: t(1)=active inhalation, during which the patient's lungs are expanding; t(2)=inhalation hold, during which the lungs remain expanded; t(3)=active exhalation; and t(4)=rest. In the illustrated embodiment, the rollers 22 are reciprocated at a rate which approximates the desired breathing rate. As noted previously, the instant invention can be used to kinesthetically produce desired rates for any psycho/physiological phenomenon, including heart rate, breath rate, blood pressure, etc. or as an alarm "touch" signal whose rate is predetermined. Rates can also be programmably reactivated or deactivated to produce desired effects. In particular, the rollers 22 are moved in the pattern illustrated in FIG. 5, wherein point A represents the position of the rollers 22 at the beginning of a forward stroke, and point B represents the position of the rollers 22 at the end of the stroke. Preferably, inhalation is represented by a forward stroke (e.g., moving the rollers 22 away from the motor 46), and exhalation is represented by a reverse stroke, such that in FIG. 5: t(1)=forward stroke (active inhalation); t(2)=rest (inhalation hold); t(3)=reverse stroke (active exhalation); and t(4)=rest.

The control unit 18 includes a control console for setting and displaying operating parameters. An exemplary stand-alone control console 60, which is microprocessor based, for use in a hospital setting is illustrated in FIG. 6. The console 60 has an electrical conduit 61 for obtaining signals from the ventilator 12 and/or from an auxiliary source, and an electrical conduit 63 for sending signals to the kinesthetic device 14 (i.e., signals for controlling the temperature of the heating elements 50 and signals for controlling the motion of the rollers 22). Since the console 60 is microprocessor based, it is also configurable to the different signal configurations for different ventilators or other equipment, and can be programmed flexibly. The console 60 also includes a timing means (not shown) for timing the operations of motor 46 to reciprocate the movable head unit 32 through time periods t(1) through t(4).

Preferably, the console 60 has an AC/DC converter such that electrical power for the kinesthetic device 14 can be supplied from the hospital's conventional AC power outlets. An analog-to-digital conversion device is also connected to conduit 61 in the event that the console 60 is used with an analog ventilator. A removable/rechargeable battery pack 52 (FIG. 1) is also provided such that the system can be used without access to AC-power, such as during field use. When the device 14 is to be used in the field, a control console 62 (FIG. 7) is preferably incorporated into the top of the device 14.

The transition from field to hospital use can be easily accomplished by simply plugging the kinesthetic device 14 into the console 60 connected, for example, to a ventilator thereby overriding console 62. Alternatively, the console 62 can be synchronized without direct connection to the ventilator. The console 62 is protected by a hinged cover 63.

Figure 8:
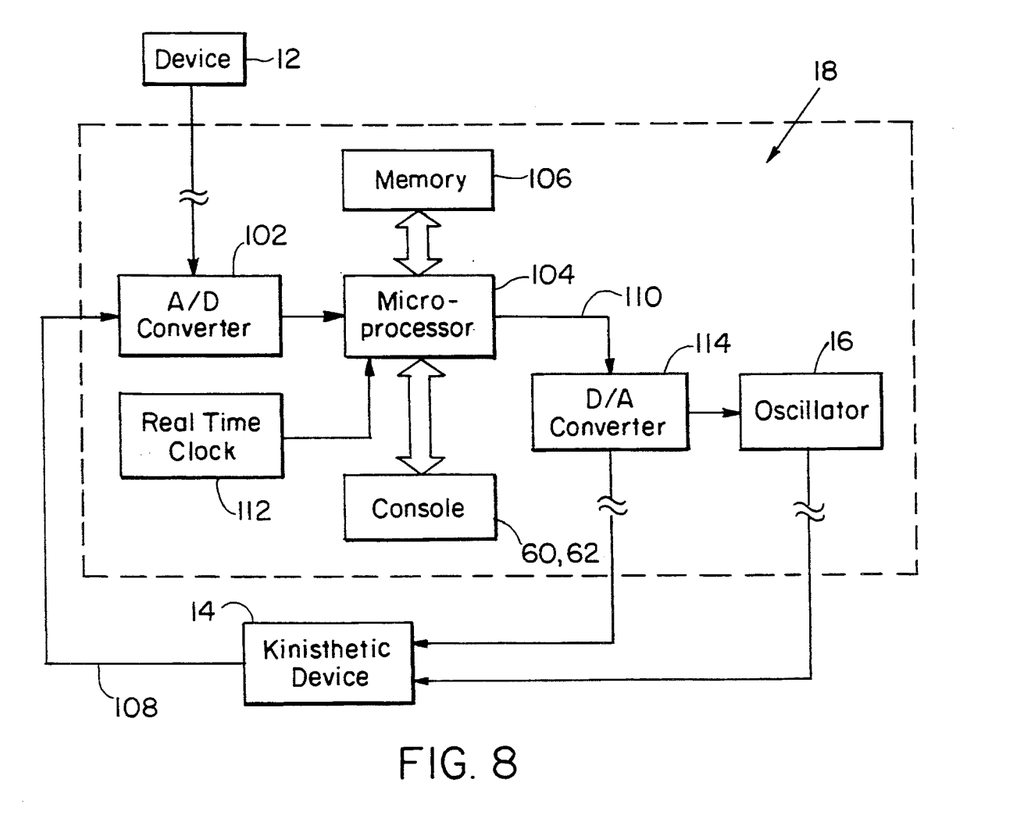
FIG. 8 is a block schematic diagram of the control unit.

Details of the controller 18 are shown in FIG. 8. The controller 18 receives inputs from a monitoring device 12, such as a ventilator, a heart rate monitor, or any other psycho/physiological measuring device. The controller 18 can also be programmed to operate without the monitoring device 12. However, when used with device 12, the output from that device is converted into a digital signal by an analog-to-digital converter 102. The digital output is then supplied to a microprocessor 104. The microprocessor 104 is programmed to translate the digital input in accordance with pre-set levels provided by the operator through console 60, 62 and stored in memory 106. In addition to levels, the memory 106 contains manufacturer signal specifications that enable microprocessor 104 to effectively operate with more than one device 12. Thus, memory 106 would contain, for example, signal information for different ventilator models enabling the controller 18 to be compatible across a wide spectrum of different ventilators.

The microprocessor 104 also receives feedback signals from the kinesthetic device 14. These signals can represent the temperature of the elements 50, the speed of the motor 46, the status of the battery 52 and/or the pressure applied by the rollers 22. The feedback signals are used by the microprocessor 104 to adjust, terminate or initiate control signals to device 14 through control line 110.

A real time clock 112 also is provided which provides time and date information to the microprocessor, to effect control, such as to set an alarm in advance.

The control output 110 is provided to a digital to analog converter 114. If the control signal relates to controlling motor 46, then the converted analog signal is switched to oscillator 16 which provides the driving voltage to motor 46 in device 14.

Preferably, the device 14 can be selectively operated in different modes. In a BPM mode, only the desired or optional breaths-per-minute are input into the device 14 and the four segments (t(1)–t(4)) of each cycle are proportionally determined according to a standard breathing pattern. In a manual control mode, each of the segments (t(1)–t(4)) is manually input into the device 14 by an operator. The device 14 may also be operated in an automatic or preset mode at a standard breaths-per-minute rate and with standard segments (t(1)–t(4)).

The illustrated kinesthetic devices can be used in emergency, surgical and postoperative settings, and in non-medical settings in connection with providing a kinesthetic effect having a predetermined rate to achieve a desired impact on a user. Thus, the present invention is not limited to use with a ventilator. It can be used, for example, as a breathing coach for a mother undergoing labor or as a classroom teaching aid for expectant parents practicing Lamaze-type breathing techniques.

The invention can also be used in occupational and/or sports therapy for improving recovery/performance by regulating the patient's breathing or for training for athletic competition in order to train athletes to regulate their breathing. The invention may also be used for musical training exercises for singers and for instrumentalists and the invention can also be used to focus appropriate rhythmic breathing for a treadmill, for an EKG monitor, for an oxygen tank, to aid in the treatment of emphysema, to assist in a patient's recovery from polio, and for anxiety/panic physiology control. The device can also promote and/or initiate breathing for infants who are susceptible to Sudden Infant Death Syndrome. The device can also be used as a preventive for anxiety/stress control to reduce heart rate and blood pressure, to reduce hyperventilation, to promote relaxation and/or sleep and to reduce emotional sequela from defibrillator action.

The systems described herein may advantageously be used in coordination with oscillator-based devices, tone frequency modulators, sub-harmonic generators, music, electromagnetic devices, acupuncture and/or alpha wave controllers in order to further calm the patient and promote the desired rhythmic breathing pattern or other desired rates.

The present invention is not limited to the systems shown and described herein. The Kinesthetic systems can include mechanical motion devices or devices having stationary arrays of transducers.

The mechanical devices can include a series of transducers which are typically rollers such as plastic rods, tubes, etc. to directly deliver a tactile sense of touch to the surface of the users skin. The plastic rollers can be sterilized as well as disposable. The stimulation is applied to the skin by moving the series of transducers over the surface of the skin in a mechanical manner dictated by a software program, hardware and feedback signal which determines the position, motion, level, and composition of the stimulation applied to the surface of the skin.

The array devices employ an array or "cluster" of electronic or mechanical devices such as audio speakers, vibrators, etc. designed to directly deliver a tactile sense of touch to the surface of the user's skin in a fixed location. The feeling of motion and touch is simulated by switching on and off individual or groups of transducers located on or near the skin surface. This changes the user's sense of position, motion, level, and composition of the stimulation applied to the surface of the skin. The operation of the transducers is controlled by a software program, hardware and feedback signal.

The devices perform their intended function when placed on or near the skin surface. The devices can have different surface textures of the material contacting the skin to change the "feel" of the device to the user. Specific transducers can be used to induce any combination of motion, audio frequencies, air flow, temperature, pressure electrical stimulation, or any other method of stimulation that can be delivered by electrical or mechanical means.

The devices can be completely controlled by a software program that drives a programmable controller, analog and digital I/O, and different transducers, motors, etc. used for positioning the transducers on the user's skin to stimulate an intended area.

The devices are also capable of accepting one or more feedback signals as input to determine and/or vary its mode of operation. The feedback signal could come from any source including the user or supervisor adjusting a knob or switch, a signal from another piece of equipment such as a monitoring device for blood pressure, temperature, respiration, or an input from a pre-recorded signal such as an audio tape. The scope of the invention is to be determined according to the following claims.

What is claimed is:

1. A method of encouraging a desired breathing pattern, said method comprising the steps of:
   providing a respiratory ventilator;
   connecting a patient to said respiratory ventilator;
   locating a kinesthetic device adjacent to said patient, the kinesthetic device being worn by the patient.
   cyclically operating said respiratory ventilator according to said desired breathing pattern; and
   cyclically operating said kinesthetic device to provide a non-driving cyclical tactile stroking stimulation to the patient in synchronization with said respiratory ventilator and thereby encouraging said patient to breath in accordance with said desired breathing pattern, the stroking stimulation emulating human touch.

2. The method of claim 2, wherein said step of locating said kinesthetic device adjacent to said patient includes the step of placing a pad in contact with the skin of said patient, said pad capable of becoming contoured in order to remain in contact with the skin of said patient and wherein said step of operating said kinesthetic device includes the step of transmitting movement across said pad in synchronization with said respiratory ventilator.

3. The method of claim 2, wherein said step of transmitting movement across said pad is performed by rollers which are operatively connected to a motor.

4. The method of claim 3, wherein said rollers are moved back and forth by a transmission system which includes a threaded shaft and a motor for rotating said threaded shaft.

5. The method of claim 4, wherein said rollers are resiliently supported by flexible rods and leaf spring supports so as to follow the contour of said pad.

6. The method of claim 2, further comprising the step of releasably attaching said kinesthetic device to said patient by flexible tape.

7. The method of claim 2, further comprising the step of replacing a covering for said kinesthetic device with another covering.

8. The method of claim 2, wherein transmitting movement across said pad in synchronization with said respiratory ventilator involves programmably adjusting said kinesthetic device to operate with different types of ventilators, treatment equipment or training equipment.

9. A system for encouraging a desired breathing pattern, said system comprising:
   a respiratory ventilator for respirating a patient according to the desired breathing pattern;
   a kinesthetic device capable of being worn by the patient having a means for providing the patient with a non-driving cyclical tactile stroking sensation, the stroking sensation emulating human touch; and
   means for cyclically operating said kinesthetic device in synchronization with said respiratory ventilator so as to encourage the patient to breath in accordance with the desired breathing pattern.

10. The system of claim 9, wherein said kinesthetic device includes a pad arranged to be in contact with the patient's skin, and means for transmitting movement through the pad in synchronization with said respiratory ventilator.

11. The system of claim 10, wherein said means for transmitting movement includes rollers, and means for moving said rollers back and forth across said pad.

12. The system of claim 11, wherein said means for moving said rollers includes a threaded shaft and a motor for rotating said threaded shaft.

13. The system of claim 12, further comprising flexible rods and leaf spring supports for resiliently supporting said rollers.

14. The system of claim 13, wherein said kinesthetic device includes means for applying heat to the patient.

15. The system of claim 14, wherein said heating means includes heating elements located within said pad.

16. The system of claim 9, wherein said means for cyclically operating further comprises a microprocessor based controller for programmably adjusting the rate of cyclical operation and for adapting said kinesthetic device to be compatible with different types of ventilators, treatment equipment or training equipment.

* * * * *